United States Patent [19]

Silvestrini

[11] Patent Number: 4,906,632

[45] Date of Patent: Mar. 6, 1990

[54] METHOD OF PREVENTING MYOCARDIAL INFARCTION AND ACUTE CEREBRAL ISCHAEMIA

[75] Inventor: Bruno Silvestrini, Rome, Italy

[73] Assignee: Aziende Chimiche Riunite Angelini Francesco A.C.R.A.F.S, Italy

[21] Appl. No.: 277,058

[22] Filed: Nov. 28, 1988

[30] Foreign Application Priority Data

Dec. 2, 1987 [IT] Italy ............... 22856 A/87

[51] Int. Cl.$^4$ ............................. A61K 31/495
[52] U.S. Cl. ..................................... 514/255
[58] Field of Search ......................... 514/255

[56] References Cited

U.S. PATENT DOCUMENTS 4,154,832  5/1979  Silvestrini .................. 514/255
4,444,778  4/1984  Coushlio ..................... 514/255

OTHER PUBLICATIONS

Failure to Central . . . Randomized Trial: Manuel Ramirez–Lessepas et al: Stroke, vol. 17, No. 5, 1986.
Experimental and . . . Acute Stroke: L. Allori et al: Current Therapeutic Research: vol. 18, No. 3, Sep. 1975.

Primary Examiner—Robert Gerstl
Attorney, Agent, or Firm—Ladas & Parry

[57] ABSTRACT

Use of trazodone for preparing pharmaceutical compositions of use in the prevention of infarction or acute cerebral ischaemia.

Controlled-release pharmaceutical compositions which, in vitro, release from 1 to 20 mg/h of trazodone base.

7 Claims, No Drawings

METHOD OF PREVENTING MYOCARDIAL INFARCTION AND ACUTE CEREBRAL ISCHAEMIA

The invention relates to a method of preventing infarction of acute cerebral ischaemia.

More particularly the invention relates to use of trazodone or a pharmaceutically acceptable acid addition salt thereof for preparing pharmaceutical compositions which, in vitro, release a quantity of trazodone, calculated as base, between 1 and 10 mg/h.

Trazodone or 2-[3-[4-(3-chlorophenyl)-1-piperazinyl]propyl]-1,2,4-triazolo[4,3-a]-pyridin-3(2H)-one is usually administered in hydrochloride form and is the subject of a wide literature. The following articles are cited by way of example: Silvestrini et al. - M.E. Goldberg (Ed.)—Pharmacological and Biochemical properties of Substances, Vol. 3, American Pharmaceutical Association (1981) and Brodgen et al. —Trazodone: a Review of its Pharmacological Properties and Therapeutic Use in Depression and Anxiety— Drugs 21, 401–476 (1981). The drug is also the subject of a number of patents. These include Italian Pat. Nos. 1,041,817 and 1,066,857, U.S. Pat. Nos. 3,381,009 and 4,154,832 and Japanese Pat. No. 555,140.

Trazodone is a known anti-depressant drug which is also described as having some usefulness in the treatment of the acute phase of cerebral stroke (L. Allori, V. Cioli and B. Silvestrini, Current Therapeutic Research, vol. 18, No. 3, 410–416) whereas another study fails to confirm the activity of trazodone in acute stroke (M. Raminez-Lessepas et al., Stroke, vol. 17, No. 5, 953–956).

It has now been found that when trazodone or a pharmaceutically acceptable acid addition salt thereof is administered to patients at risk of infarction or acute cerebral ischaemia, it can have a true prophylactic effect.

This was unexpected since trazodone was not recomended in the initial phase of convalescence after myocardial infarction and since, as it is known, there is a certain overlap between the risk factors for cerebral infarction or stroke and myocardial infarction. This was also confirmed in the clinical study referred to hereinafter, in that some episodes of infarction and cardiac ischaemia also occurred. On the other hand, trazodone also had a protective effect on the last-mentioned episodes by decreasing the frequency thereof, even though anti-depressants are usually considered as contraindicated for patients suffering from or at risk of heart disease, and in the case of trazodone itself (DESYREL (®)), the United States Health Authority (FDA) has stipulated a warning notice as follows: "It is not recommended to use DESYREL during the initial phase of convalescence after myocardial infarction".

The present invention was also unexpected since the rationale for using a drug in the prevention or in the therapy of a given pathology is completely different from one another. For example, the acute phase of infection is treated with antibiotics whereas the infection is prevented with vaccines. The fact that trazodone possesses both properties dealing with treatment of acute phase and prevention does not therefore mean that these two effects are produced by the same mechanism of action, but rather that trazodone possesses two different and clearly distinguishable effects. In fact, the two conditions have different anatomopathological and biochemical bases and imply different mechanism of action. The activity of trazodone in the acute phase of stroke has been ascribed to its antiserotonin properties, as it is known that serotonin is released around the ischemic area and contributes to altering blood circulation and damaging brain tissue.

These properties, however, cannot be responsible for the activity of trazodone in the prevention of stroke and heart ischaemia.

One further object of the invention is therefore the use of trazodone or an acid addition salt thereof for preparing pharmaceutical compositions of use in the prevention of infarction and acute cerebral ischaemia.

It has also been found that the best results are obtained when trazodone has both a central and a peripheral effect, and to this end it is preferable for blood levels to be constant and prolonged in time.

The preferred dose is that obtained when patients at risk are given controlled-release pharmaceutical forms which, when subjected to the dissolving test in vitro, release from 1 to 10 mg/h, or even more preferably 1.5 to 7 mg/h of trazodone calculated as base.

The invention therefore also relates to controlled release pharmaceutical forms which in vitro release from 1 to 10 mg/h of trazodone base.

The pharmaceutical forms according to the invention can be prepared by any of the many known galenic methods including those suitable for preparing controlled-release pharmaceutical forms. In the latter case it is preferred to use one of the methods for bringing about timed release of a quantity of trazodone, calculated as base, within the previously-given limits.

The non-active ingredients may also be chosen as desired from among those known to the skilled addressee as being the most suitable, depending on the chosen method of preparation.

There is also no limit with regard to the dosage of the active ingredient in each dosage unit. Preferably, however, the amount of active ingredient in each unit is such as to bring about release in vitro of the desired quantity of trazodone base for at least 6 hours.

Capsules, tablets and dragees are examples of preferred dosage units. However, use can also be made of pharmaceutical forms suitable for injection or rectal adminitration.

The tests for determining the amount of active ingredient released by the pharmaceutical forms according to the invention are those described in the Farmocopea Ufficiale Italiana or other tests of comparable authority.

The following formulation non-limitatively illustrates the invention.

| COATED TABLES | |
|---|---|
| The core of each tablet contains: | |
| Trazodone hydrochloride | 50 mg |
| Carnauba Wax | 8 mg |
| Caster sugar | 28 mg |
| Povidone | 8 mg |
| Magnesium stearate | 2 mg |
| The suspension used for coating 100 000 cores contains: | |
| Hydroxy propyl methyl cellulose | 300 g |
| Propylene glycol | 100 g |
| Sorbitan monolaurate | 100 g |
| Erythrosine, lake | 1.25 g |
| Indigo carmine, lake | 2 g |
| Titanium dioxide | 25 g |
| Purified water q.s. ad | 5000 ml |

The aforementioned coated tablets were prepared by traditional methods and dissolve in the following times:

-continued

COATED TABLES

| 4 h | 25–55% |
|---|---|
| 8 h | 50–80% |
| 12 h | 75–95% |
| 24 h | 85–100% |

For the purpose of the clinical study described hereinafter, a placebo was also prepared, i.e. coated tablets identical with the preceding in all respects except that trazodone hydrochloride was replaced by the same quantity of lactose.

The study was carried out on patients who, on the basis of previous study, were diagnosed as having a 30% risk of a stroke, i.e.:

(a) patients with recent ischaemia (<2 weeks) and transmural myocardial infarction and/or angina pectoris and/or arrhythmia produced by embolism during the preceding six months;
(b) patients with recent ischaemia (<2 weeks) with complex or stenosing unilateral lesion in the symptomatic carotid (also shown by doppler sonography) unsuitable for endoarteriectomy;
(c) patients with two or more recent attacks of ischaemia (<2 weeks) in the same carotid area;
(d) patients with bilateral stenosing artherosclerotic lesions or multiple intra- and extra-cranial disease:

(1) for surgical operation;
(2) inoperable; and (e) patients for substitution of two or more heart valves or multiple coronary bypass intervention, with proved carotid disease (also shown by doppler sonography) and/or who had shown symptoms of transitory focal ischaemia.

The study was made under double-blind conditions in accordance with a randomised block pattern.

The coated tablets used contained 50 mg of trazodone hydrochloride or placebo having the composition stated hereinbefore and made up in identical, indistinguishable manner.

The drug or placebo were administered for about a year in accordance with the following pattern:
(a) Non-surgical patients were given tablets in accordance with the following dose pattern:
first two days under study: 1 tablet in the evening;
third and fourth days: 1 tablet in the morning and one in the evening;
fifth day: 1 tablet in the morning and two in the evening.

The tablets were taken after meals. In the case of intolerance of the maximum dose, a return was made to the preceding dose.
(b) Surgical patients were given ampoules containing a dose of 1 ampoule twice a day for two days by slow venous perfusion when it was intended to operate on the third day under study. In other cases, pattern (a) was followed.

After the operation, oral treatment was given (one tablet in the morning and two in the evening) until the end.

About 176 patients were admitted for the study and completed the treatment cycle of about a year. Among them, a total of 42 pathological events were observed.

The following Table shows the distribution of these events in accordance with the "at risk" diagnostic category, and the experimental treatment.

Out of 82 patients treated with the placebo, there were 30 events, at a frequency of 32.6%, in line with theoretical predictions for selected patients at risk.

Among the 94 patients treated with trazodone there were 12 events with a frequency of 12.85, which is less than half that predicted for patients at risk.

The different between the frequency of the events in the two experimental groups is statistically significant ($X_1^2$ 9.367: $p<0.01$).

It is therefore concluded that trazodone brought about a more than 50% reduction in pathological vascular events in patients at risk.

Another subject of the invention therefore is a method of preventing infarction and acute cerebral ischaemia, characterised in that patients at risk are given a pharmaceutical composition containing trazodone or an acid addition salt thereof.

|  |  | TRAZODONE |  |  |  |  | PLACEBO |  |  |  |  |
|---|---|---|---|---|---|---|---|---|---|---|---|
|  |  |  | EVENT |  |  |  |  | EVENT |  |  |  |
| DIAGNOSIS | TOT. CASE | No. CASES | ICTUS | ISCHAE. MYOC. | INF. MYOC. | TOTAL | No. CASES | ICTUS | ISCHAE. MYOC. | INF. MYOC. | TOTAL |
| (a) | 19 | 10 | 3 | — | — | 3 | 9 | 3 | — | — | 4 |
| (b) | 14 | 7 | — | — | — | — | 7 | 1 | — | 1 | 2 |
| (c) | 47 | 24 | 4 | — | — | 4 | 23 | 5 | 1 | — | 9 |
| (d$_1$) | 54 | 26 | 2 | — | 1 | 3 | 28 | 3 | 2 | 1 | 9 |
| (d$_2$) | 29 | 15 | — | 1 | — | 1 | 14 | 1 | 1 | — | 4 |
| (e) | 23 | 12 | 1 | — | — | 1 | 11 | 1 | — | — | 2 |
| Total | 176 | 94 | 10 | 1 | 1 | 12 | 82 | 14 | 4 | 2 | 30 |

Preferably use is made of a controlled-release composition which in vitro releases from 1 to 10 mg/h of trazodone calculated as base. Even more preferably the aforementioned controlled-release compositions release in vitro from 1.5 to 7 mg/h of trazodone calculated as base.

I claim:

1. A method of preventing myocardial infarction and acute cerebral ischaemia comprising administering an effective amount of trazodone to a patient at risk for acute cerebral ischaemia or myocardial infarction.

2. The method, as in claim 1 wherein the trazodone is administered in a composition further comprising a pharmaceutically acceptable carrier.

3. The method, as in claim 2 wherein the composition comprises a controlled release pharmaceutical composition which in vitro releases 1–10 mg/h of trazodone calculated as base.

4. The method, as in claim 3 wherein the controlled release composition releses 1.5–7 mg/h of trazodone.

5. The method, as in claim 2 wherein the trazodone is administered daily for one year.

6. The method, as in claim 5 wherein the effective amount comprises one 50 mg dose of trazodone taken each morning, and two 50 mg doses each evening.

7. The method, as in claim 2 wherein the trazodone is administered orally or parenterally.

* * * * *

UNITED STATES PATENT AND TRADEMARK OFFICE
CERTIFICATE OF CORRECTION

PATENT NO. : 4,906,632

DATED : March 6, 1990

INVENTOR(S) : Bruno SILVESTRINI

It is certified that error appears in the above-identified patent and that said Letters Patent is hereby corrected as shown below:

Title Page, Column 1, Item [73] Assignee --

Please change "A.C.R.A.F.S." to -- A.C.R.A.F. S.P.A. --.

Signed and Sealed this

Twenty-eighth Day of April, 1992

Attest:

HARRY F. MANBECK, JR.

*Attesting Officer*  *Commissioner of Patents and Trademarks*